United States Patent [19]

Varma et al.

[11] 4,113,722
[45] Sep. 12, 1978

[54] STEROIDAL[16a,17-b]BENZODIOXINS

[75] Inventors: Ravi K. Varma, Belle Mead; Christopher M. Cimarusti, Hamilton, both of N.J.

[73] Assignee: E. R. Squibb & Sons, Inc., Princeton, N.J.

[21] Appl. No.: 850,514

[22] Filed: Nov. 11, 1977

[51] Int. Cl.$^2$ ................................................ C07J 5/00
[52] U.S. Cl. ......................................... 260/239.55 R
[58] Field of Search ............................... 260/239.55 R

[56] References Cited

U.S. PATENT DOCUMENTS 3,971,772  7/1976  Cimarusti et al. .......... 260/239.55 R
3,971,773  7/1976  Cimarusti et al. .......... 260/239.55 R Primary Examiner—Elbert L. Roberts
Attorney, Agent, or Firm—Lawrence S. Levinson; Merle J. Smith; Donald J. Barrack

[57] ABSTRACT

Steroids having the formula

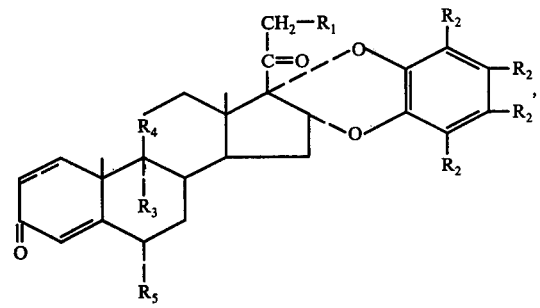

wherein $R_1$ is hydrogen, acyloxy, halogen or alkoxy of 1 to 10 carbons; $R_2$ is halogen or cyano; $R_3$ is hydrogen or halogen; $R_4$ is carbonyl, β-hydroxymethylene or β-acetyloxymethylene; and $R_5$ is hydrogen or fluorine; can be used as antiinflammatory agents.

16 Claims, No Drawings

STEROIDAL[16α,17-b]BENZODIOXINS

RELATED APPLICATION

Copending U.S. patent application Ser. No. 796,293, filed May 12, 1977, by Ravi K. Varma discloses 17-alkylthio (and arylthio)androsteno[16α,17α-b]benzodioxin-3-ones as antiinflammatory agents.

BACKGROUND OF THE INVENTION

Many steroids of the pregnene series are known to have antiinflammatory activity. More particularly, steroids of the pregnene series having heterocyclic rings fused in the 16,17-positions are known. U.S. Pat. No. 3,971,772, issued July 27, 1976, discloses steroidal [16α,17-b][1,4]dioxanes and steroidal[16α,17-b][1,4]dioxins. U.S. Pat. No. 3,971,773, issued July 27, 1976 discloses steroidal 9,11-dihalo[16α,17-b][1,4]dioxanes and steroidal 9,11-dihalo[16α,17-b][1,4]dioxins. The steroids described in both patents are steroids of the pregnene series that are useful as antiinflammatory agents. Neither reference discloses a steroid having a substituted or unsubstituted benzodioxin substituent fused in the 16,17-position.

SUMMARY OF THE INVENTION

Steroids having the formula

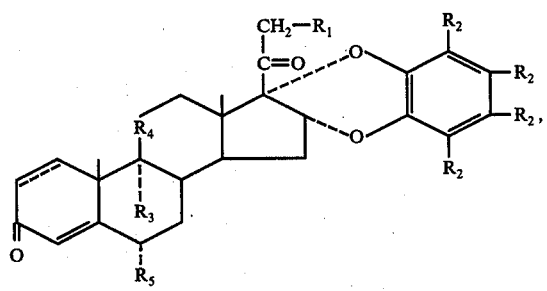

can be used as antiinflammatory agents. In formula I, and throughout the specification, the symbols are as defined below.

$R_1$ is hydrogen, acyloxy, halogen or alkoxy of 1 to 10 carbon atoms;

$R_2$ is halogen or cyano;

$R_3$ is hydrogen or halogen;

$R_4$ is carbonyl, β-hydroxymethylene or β-acetyloxymethylene; and $R_5$ is hydrogen or fluorine.

A dotted line in the 1,2 position of a structural formula in this disclosure indicates the optional presence of ethylenic unsaturation.

The term "halogen", as used throughout the specification, refers to fluorine, chlorine, bromine and iodine.

The term "acyloxy," as used throughout the specification, refers to a group having the formula

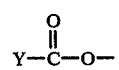

wherein Y is alkyl of 1 to 10 carbon atoms or phenyl.

DETAILED DESCRIPTION OF THE INVENTION

The steroids of this invention can be prepared utilizing as starting materials $\Delta^{16}$-pregnenes having the formula

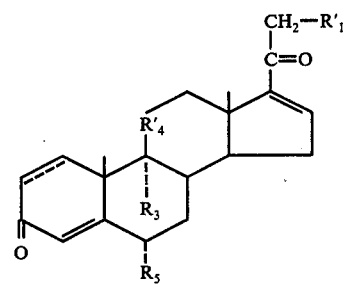

In formula II, and throughout the specification, $R'_1$ is hydrogen, acyloxy or halogen and $R'_4$ is carbonyl or β-hydroxymethylene.

A steroid of formula II wherein $R'_4$ is β-hydroxymethylene can be reacted with a mixture of acetic acid and acetic anhydride in the presence of an acid catalyst such as p-toluenesulfonic acid, followed by the addition of an acetate salt, to yield the corresponding 11β-acetyloxy steroid having the formula

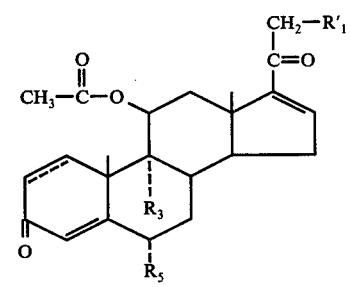

Reaction of a $\Delta^{16}$-pregnene of formula II or III with an organic base and trimethylchlorosilane, an organic base and trimethylsilyltrifluoromethane sulfonate or bistrimethylsilyltrifluoroacetamide, yields a 20-trimethylsilyl enol ether pregnene having the formula

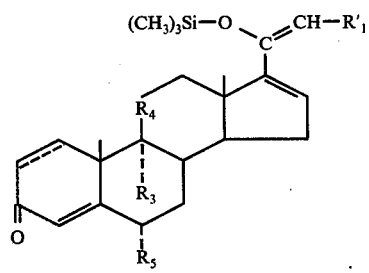

When the $\Delta^{16}$-pregnene reactant is an 11β-hydroxy steroid of formula II, the reaction also yields (as a minor product) a steroid having the formula

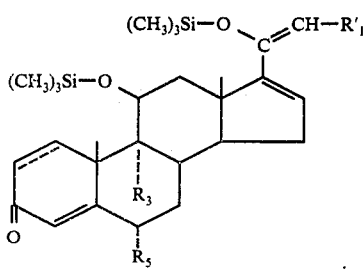

Reaction conditions are not critical, but the reaction proceeds more rapidly when the reactants are maintained at a temperature of about 110°–115° C.

An intermediate of formula IV can be reacted with an o-benzoquinone having the formula

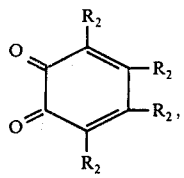

preferably at room temperature, and then treated with an aqueous acid to yield a steroid product having the formula

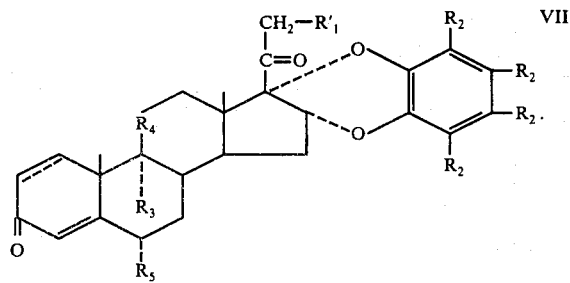

When preparing a steroid of formula VII wherein $R_4$ is β-hydroxymethylene, it is convenient to use the crude mixture of intermediates IV (wherein $R_4$ is β-hydroxymethylene) and V to react with the o-benzoquinone. This will result in a mixture of steroids comprising, in addition to a steroid of formula VII (wherein $R_4$ is β-hydroxymethylene), a steroid having the formula

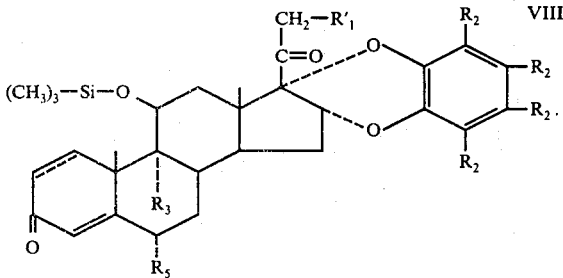

The product of formula VII can be isolated from the mixture using conventional separation techniques.

Those steroids of formula I wherein $R_1$ is alkoxy of 1 to 10 carbon atoms can be prepared by reacting a corresponding 21-halo steroid of formula VII with the appropriate lower alkanol having 1 to 10 carbon atoms and a base such as an alkali metal carbonate.

Modifications of the above-described processes for preparing the steroids of formula I will be apparent to the person of ordinary skill in the art. For example, the 11β-acetyloxy steroids of formula I can be prepared by acylating the corresponding 11β-hydroxy steroid of formula I. Those steroids of formula I wherein $R_1$ is alkoxy can be prepared by converting a 21-halo-$\Delta^{16}$-pregnene of formula II to a 21-alkoxy-$\Delta^{16}$-pregnene and then proceeding as described above.

The by-products of formula VIII can be converted to the corresponding 11β-hydroxy steroids of formula I. As such, they are valuable intermediates, and an integral part of this invention. The conversion is carried out in an organic solvent (e.g., tetrahydrofuran) at a reduced temperature (about −78° C.) and comprises adding a quaternary fluoride base, such as tetrabutylammonium fluoride, to the 11β-trimethylsilyl ether of formula VIII.

The steroids of formula I can be used in lieu of known glucocorticoids in the treatment of inflammatory conditions; e.g., rheumatoid arthritis. They can be administered in the same manner as hydrocortisone, the dosage being adjusted for the relative potency of the particular steroid. Additionally, the steroids of this invention can be used topically in lieu of known glucocorticoids in the treatment of skin conditions such as dermatitis, psoriasis, sunburn, neurodermatitis, eczema or anogenital pruritus.

When given orally, the steroids of this invention may be used in a dosage range of 0.1 to 200 milligrams, preferably 0.3 to 100 milligrams, for a 70 kg. mammal. If administered topically, the steroids of this invention may be used in the range of 0.01 to 5.0% by weight, preferably 0.05 to 2.0% by weight, in a conventional cream, ointment, lotion or the like.

The following examples are specific embodiments of this invention.

EXAMPLE 1

11β-(Acetyloxy)-5′,6′,7′,8′-tetrachloro-9-fluoro-2′,3′-dihydropregna-1,4-dieno[16α,17-b][1,4]benzodioxin-3,20-dione (A) 11β-(Acetyloxy)-9-fluoropregna-1,4,16-triene-3,20-dione A solution of 9-fluoro-11β-hydroxypregna-1,4,16-triene-3,20-dione (1.0g) in a mixture of acetic acid (70 ml) and acetic anhydride (70 ml) containing p-toluenesulfonic acid hydrate (500 mg) is stirred at room temperature for 60 hours. Sodium acetate (2.0g) is added and the mixture is concentrated in vacuo. The residue is mixed with water and washed with a dilute sodium bicarbonate solution and water, dried and the residue is crystallized from ethyl acetate-hexane to afford 0.9g of the title compound, melting point 202°–203° C.

(B) 11β-(Acetyloxy)-9-fluoro-20-trimethylsilyloxypregna-1,4,16,20-tetraene-3-one A solution of 11β-acetyloxy-9-fluoropregna-1,4,16-triene-3,20-dione (77 mg) in dry acetonitrile (1.0 ml) containing bis-trimethylsilyltrifluoroacetamide (0.3 ml) and trimethylchlorosilane (0.05 ml) is heated in a closed pressure vial in a bath at 110° C. for 17 hours. The mixture is evaporated in vacuo and the residue is crystallized from ethyl acetatehexane to afford 40 mg of the title compound as a solid.

(C) 11β-(Acetyloxy)-20-trimethylsilyloxy-5',6',7',8'-tetrachloro-9-fluoro-2',3'-dihydropregna-1,4,20-trieno[16α,17-b][1,4]benzodioxin-3-one A solution of 11β-(acetyloxy)-9-fluoro-20-trimethylsilyloxypregna-1,4,16,20-tetraene-3-one (28 mg) in dry toluene (4.0 ml) is mixed with tetrachloro-o-benzoquinone (15 mg) and let stand at room temperature. It is concentrated in vacuo and the residue is purified by preparative thin-layer chromatography on silica gel plates using chloroform-ethyl acetate (7:3) for development to afford 15 mg of the title compound as a solid, which is characterized by its nmr spectrum.

(D) 11β-(Acetyloxy)-5',6',7',8'-tetrachloro-9-fluoro-2',3'-dihydropregna-1,4-dieno[16α,17-b][1,4]benzodioxin-3,20-dione A solution of 11β-(acetyloxy)-20-trimethylsilyloxy-5',6',7',8'-tetrachloro-9-fluoro-2',3'-dihydropregna-1,4,20-trieno[16α,17-b][1,4]benzodioxin-3-one (14 mg) in 90% methanol (0.5 ml) is mixed with 1.0N hydrochloric acid (0.05 ml). After 1.0 hour, the solution is diluted with water, and the product is isolated by extraction with chloroform. The chloroform solution is dried, evaporated and the residue is crystallized from ethyl acetate-hexane to afford 9.0 mg of the title compound as a solid, which is characterized by its nmr spectrum.

EXAMPLE 2

11β,21-bis-(Acetyloxy)-5',6',7',8'-tetrachloro-9-fluoro-2',3'-dihydropregna-1,4-dieno[16α,17-b][1,4]benzodioxin-3,20-dione (A) 11β,21-bis-(Acetyloxy)-9-fluoropregna-1,4,16-triene-3,20-dione A suspension of 21-(acetyloxy)-9-fluoro-11β-hydroxypregna-1,4-diene-3,20-dione (25 g) in a mixture of acetic acid (60 ml) and acetic anhydride (60 ml) containing p-toluenesulfonic acid hydrate (7.5 g) is stirred at room temperature for 60 hours. Sodium acetate (15 g) is added and the mixture is concentrated in vacuo. The resulting solid is washed well with water and then dried, yielding 31 g of material. The solid is dissolved in dry dimethylformamide containing fused potassium acetate (17 g), the mixture is stirred at 120° C. for 4.5 hours and poured into water. The separated solid is isolated by filtration, dried and crystallized from dichloromethane-methanol to yield 18.2g of the title compound, melting point 294°–296° C.

(B) 11β,21-bis-(Acetyloxy)-9-fluoro-20-trimethylsilyloxypregna-1,4,16,20-tetraene-3-one A solution of 11β,21-bis(acetyloxy)-9-fluoropregna-1,4,16-triene-3,20-dione (3.0g) in dry dimethylformamide (20 ml) containing bis-trimethylsilyltrifluoroacetamide (6.0 ml) and trimethylchlorosilane (60 μl) is heated in a pressure vial in a bath at 115°–120° C. for 12 hours. The mixture is cooled, poured into an excess of saturated sodium bicarbonate solution and extracted with dichloromethane. The dichloromethane solution is washed with cold water, dried, evaporated and the residue crystallized from ethyl acetate-hexane to afford 1.22 g of the title compound as a solid which is characterized by its nmr spectrum.

(C) 11,21-bis(Acetyloxy)-5',6',7',8'-tetrachloro-9-fluoro-2',3'-dihydro-20-trimethylsilyloxypregna-1,4,20-trieno[16α,17-b][1,4]benzodioxin-3-one To a solution of 11β,21-bis(acetyloxy)-9-fluoro-20-trimethylsilyloxypregna-1,4,16,20-tetraene-3-one (696 mg) in dry dichloromethane (15 ml) is added a solution of tetrachloro-o-benzoquinone (302 mg) in dry dichloromethane. An NMR analysis of the residue after evaporation of the solvent showed the reaction mixture to contain the title compound in an amount of about 45%. This mixture is used in the next step without further purification.

(D) 11,21-bis(Acetyloxy)-4',6',7',8'-tetrachloro-9-fluoro-2',3'-dihydropregna-1,4-dieno[16α,17-b][1,4]benzodioxin-3,20-dione The impure 11,21-bis(acetyloxy)-5',6',7',8'-tetrachloro-9-fluoro-2',3'-dihydro-20-trimethylsilyloxypregna-1,4,20-trieno[16α,17-b][1,4]benzodioxin-3-one (900 mg) prepared as described above, is dissolved in a mixture of 1,2-dimethoxyethane (10 ml) and 75% acetic acid (10 ml) and is heated in a bath at 100° C. for 1.5 hours. The solution is then cooled, diluted with water and extracted with chloroform. The chloroform extracts are combined, washed with a dilute sodium bicarbonate solution and water, dried, evaporated and the residue subjected to preparative thin-layer chromatography on silica gel plates (using chloroform-methanol, 97:3, for development) to isolate 260 mg of the title compound, melting point 273°–274° C.(dec.)

EXAMPLE 3

5',6',7',8',21-Pentachloro-9-fluoro-2',3'-dihydro-11β-hydroxypregna-1,4-dieno[16α,17-b][1,4]benzodioxin-3,20-dione (A) 9-Fluoro-11β-hydroxy-21-methanesulfonyloxypregna-1,4,16-triene-3,20-dione A solution of 16 grams of 9-fluoro-11β,21-dihydroxypregna-1,4,16-triene-3,20-dione in dry pyridine (200 ml) is reacted with methanesulfonyl chloride (5.0 ml) for 2 hours at 0° C. The mixture is poured into an excess of cold 2N-hydrochloric acid. The solid that separates from the resulting solution is isolated yielding 17.5g of the title compound, which is characterized by its nmr spectrum.

(B) 21-Chloro-9-fluoro-11β-hydroxypregna-1,4,16-triene-3,20-dione

To a solution of 17.5g of 9-fluoro-11β-hydroxy-21-methanesulfonyloxypregna-1,4,16-triene-3,20-dione in dry dimethylformamide (250 ml) is added lithium chloride (30g). The mixture is heated, with stirring, from 30° to 100° C. over a 30-minute period. It is cooled and poured into cold water (1.51) and the precipitated solid is isolated and crystallized from methanol to afford 12g of the title compound, melting point 258°–260° C.(dec.).

(C) 21-Chloro-9-fluoro-11β-hydroxy-20-trimethylsilyloxypregna-1,4,16,20-tetraene-3-one A solution of 21-chloro-9-fluoro-11β-hydroxypregna-1,4,16-triene-3,20-dione (456 mg) in dry dimethylformamide (9.0 ml) containing 1.2 ml of bis(trimethylsilyl)trifluoroacetamide (Regisil®, Regis Chemical Company; contains 1% trimethylsilyl chloride) is heated in a tightly stoppered flask for 1.0 hour in a bath at 110°–116° C. The solution is cooled, poured into dilute sodium bicarbonate solution and the steroid product is extracted into chloroform. The chloroform solution is washed several times with cold water, dried and evaporated to a gum that contains traces of dimethylformamide. (By dissolving this gum in ethyl acetate and diluting the solution with hexane, it is possible to isolate homogeneous 21-chloro-9-fluoro-11β-hydroxy-20-trimethylsilyloxypregna-1,4,16,20-tetraene-3-one). The nmr spectrum shows the gum to be essentially a mixture of the title compound, the 11β-trimethylsilyl derivative of the title compound and small amounts of other impurities.

(D) 5',6',7',8',21-Pentachloro-9-fluoro-2',3'-dihydro-11β-hydroxypregna-1,4-dieno[16α,17-b]benzodioxin-3-one The impure 21-chloro-9-fluoro-11β-hydroxy-20-trimethylsilyloxypregna-1,4,16,20-tetraene-3-one prepared as described above is dissolved in dry dichloromethane (15 ml) and a solution of tetrachloro-o-benzoquinone (312 mg) in dry dichloromethane is added. After 24 hours at room temperature, the solution is diluted with methanol (10 ml), 5% hydrochloric acid (0.3 ml) is added and the solution is kept at room temperature for 1.0 hour. The solution is then poured into water and the products are isolated by extraction with chloroform. The chloroform extract is washed with water, dried and the residue is subjected to preparative thin-layer chromatography on silica gel plates using chloroform-ethyl acetate (8:2) for development to isolate 460 mg of the title compound and 218 mg of the 11β-trimethylsilyl derivative of the title compound. Two crystallizations of the 460 mg material from acetone-hexane yields 50 mg of the title compound, melting point 300°–302° C.(dec., discoloration starts long before melting).

EXAMPLE 4

21-(Acetyloxy)-5',6',7',8'-tetrachloro-9-fluoro-2',3'-dihydro-11β-hydroxypregna-1,4-dieno[16α,17-b][1,4]benzodioxin-3,20-dione (A) 21-(Acetyloxy)-9-fluoro-11β-hydroxy-20-trimethylsilyloxypregna-1,4,16,20-tetraene-3-one A solution of 21-(acetyloxy)-9-fluoro-11β-hydroxypregna-1,4,16-triene-3,20-dione (2.1g) in dry dimethylformamide and 7.0 ml of bis(trimethylsilyl)trifluoroacetamide (Regisil ®, Regis Chemical Company; contains 1% trimethylsilyl chloride) is heated in a tightly stoppered flask at 110°–115° C. for 3.0 hours. An additional 2.0 ml of Regisil ® is added and heating is continued for an additional hour. The solution is cooled and is added into a vigorously stirred 15% sodium bicarbonate solution (200 ml). The steroid product is then isolated by extraction with chloroform, washed with cold water, dried and evaporated to yield 3.1g of a gum. On the basis of the NMR spectrum and thin-layer chromatography behavior, it is determined that this gum is mainly a mixture of the title compound and its 11β-trimethylsilyl derivative.

(B) 21-(Acetyloxy)-5',6',7',8'-tetrachloro-9-fluoro-2',3'-dihydro-11β-hydroxypregna-1,4-dieno[16α,17-b][1,4]benzodioxin-3,20-dione The above gum (3.1 g) is dissolved in dry dichloromethane (20 ml) and a solution of tetrachloro-o-benzoquinone (1.06 g, 4.33 mmole) in dry dichloromethane (7 ml) is added. The solution is allowed to stand at room temperature for 20 hours. It is then evaporated in vacuo, mixed with dimethoxyethane (20 ml) and 75% acetic acid (10 ml), and heated in a bath at 100°–105° C. for 1.0 hour. The solution is cooled, diluted with water and extracted with chloroform. The chloroform solution is washed with a dilute sodium bicarbonate solution and water, dried (MgSO₄ anh.) and evaporated to afford a gum. The gum is chromatographed over a column of silica gel (60 g). Elution of the column with chloroform-hexane (1:1) affords 708 mg of the 11β-trimethylsilyl ether of the title compound as a foam. Further elution of the column with chloroform-hexane (3:1) and chloroform-ethyl acetate (3:1) affords 1.89g of a gum which is a mixture of four compounds.

The gum (1.89g) is exposed to acetic anhydridepyridine for 3.0 hours and the product, after work-up, is chromatographed over silica gel (40g). Elution of the column with chloroform gives 1.1g of a mixture of 21-(acetyloxy)-9-fluoro-11β-trimethylsilyloxypregna-1,4,16-triene-3,20-dione and 21-(acetyloxy)-5',6',7',8'-tetrachloro-9-fluoro-2',3'-dihydro-11β-trimethylsilyloxypregna-1,4-dieno[16α,17-b][1,4]benzodioxin-3,20-dione. Further elution with chloroform-ethyl acetate (9:1) gives 600 mg of a semi-solid which is essentially a mixture of the title compound and another compound. The mixture is subjected to preparative thin-layer chromatography on silica gel plates (development with chloroform-ethyl acetate (2:8)) to isolate 230 mg of the title compound.

A solution of 415 mg of the 11β-trimethylsilyl ether of the title compound in 5.0 ml of dry tetrahydrofuran is cooled and stirred in a bath at −78° C. To this solution is added a solution of freshly prepared and dried tetrabutylammonium fluoride (350 mg) in dry tetrahydrofuran. After 15 minutes the solution is warmed to, and maintained, in a bath at −35° to −45° C. for 1.0 hour and is then quenched with acetic acid (0.5 ml). The mixture is diluted with water and extracted with chloroform. The chloroform solution is washed with a dilute sodium bicarbonate solution and water, dried and evaporated. The residue is subjected to preparative thin-layer chromatography on silica gel plates to isolate 130 mg of the title compound.

The two crops of the title compound are combined and crystallized from ethyl acetate to afford 216 mg of the title compound, melting point 196°–199° C.

EXAMPLE 5

11β-(Acetyloxy)-5',6',7',8',21-pentachloro-9-fluoro-2',3'-dihydropregna-1,4-dione[16α,17-b][1,4]benzodioxin-3,20-dione (A) 11β-(Acetoxy)-21-chloro-9-fluoropregna-1,4,16-triene-3,20-dione A suspension of 21-chloro-9-fluoro-11β-hydroxypregna-1,4,16-triene-3,20-dione (2.1g) in a mixture of glacial acetic acid (30 ml) and acetic anhydride (30 ml) containing p-toluenesulfonic acid hydrate (2.1g) is stirred at room temperature. After 30 hours the solution is mixed with sodium acetate hydrate (5.0g) and evaporated in vacuo. The residue is dissolved in chloroform, washed with water, dried and evaporated to afford the title compound. One crystallization from acetone affords 1.85g of the title compound, melting point 222°–223° C. (dec).

(B) 11β-(Acetyloxy)-21-chloro-9-fluoro-20-trimethylsilyloxypregna-1,4,16,20-tetraene-3-one A solution of 11β-(acetyloxy)-21-chloro-9-fluoropregna-1,4,16-triene-3,20-dione (1.35g) in dry acetonitrile (20 ml) containing 3.5 ml of bis(trimethylsilyl)trifluoroacetamide (Regisil ®, Regis Chemical Company; contains 1% trimethylsilyl chloride) is heated in a pressure vial at about 150° C. for 1.0 hour. The solution is then cooled and evaporated in vacuo to leave 1.6g of the title compound contaminated with trace amounts of less polar impurities. This is used in the next step without further purification.

(C) 11β-(Acetyloxy)-5',6',7',8',21-pentachloro-9-fluoro-2',3'-dihydropregna-1,4-dieno[16α,17-b][1,4]benzodioxin-3,20-dione The crude material from the previous experiment (1.6g) is dissolved in dry dichloromethane (20 ml), mixed with a dichloromethane solution of tetrachloro-o-benzoquinone (984 mg), and the solution is left at room temperature for 18 hours. 10% Hydrochloric acid (10 ml) is added and the solution is stirred for 10 minutes. The resultant organic layer is separated, washed with a dilute sodium bicarbonate solution and water, dried and evaporated to a residue. This is subjected to column chromatography on silica gel (30g). Elution with chloroform-hexane (1:1) removes first the nonsteroidal impurities. Further elution with the same solvent system and chloroform affords 2.05g of the title compound contaminated with a more polar impurity. This material is subjected to preparative thin-layer chromatography on silica gel plates (development with chloroformethyl acetate, 9:1) to isolate 1.67g of the title compound which contains only traces of impurities. One crystallization of this from methanol affords 1.37g of the title compound, melting point 191°–193° C.

EXAMPLE 6

5',6',7',8'-Tetrachloro-9-fluoro-2',3'-dihydro-11β-hydroxy-21-methoxypregna-1,4-dieno[16α,17-b][1,4]benzodioxin-3,20-dione To a solution of 11β-(acetyloxy)-5',6',7',8',21-pentachloro-9-fluoro-2',3'-dihydropregna-1,4-dieno[16α,17-b][1,4]benzodioxin-3,20-dione (1.07g) in a mixture of methanol (20 ml) and tetrahydrofuran (20 ml) containing water (2.0 ml) is added a solution of potassium carbonate (420 mg) in water (4.0 ml). The mixture is stirred at room temperature for 2.0 hours, acidified with 5% hydrochloric acid and concentrated in vacuo. From the residue the steroid is isolated by extraction with a mixture of chloroform and ethyl acetate. The material thus obtained is subjected to preparative thin-layer chromatography on silica gel plates (development with chloroform-ethyl acetate, 3:1) to isolate 410 mg of the title compound. This is crystallized from acetone-hexane to afford 280 mg of the title compound, melting point 203°–204° C.(dec.).

What is claimed is:

1. A steroid having the formula

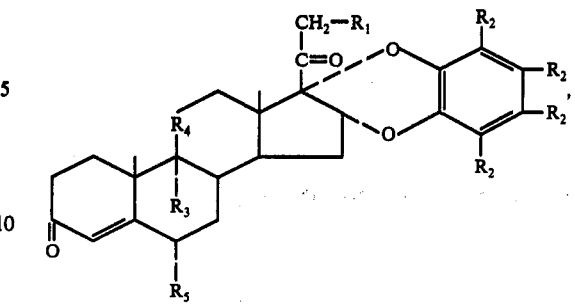

or the 1,2-dehydro derivative thereof, wherein
$R_1$ is hydrogen, halogen, alkoxy of 1 to 10 carbon atoms, or

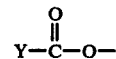

wherein Y is alkyl of 1 to 10 carbon atoms or phenyl;
$R_2$ is halogen or cyano;
$R_3$ is hydrogen or halogen;
$R_4$ is carbonyl, β-hydroxymethylene or β-acetyloxymethylene; and
$R_5$ is hydrogen or fluorine.

2. A steroid in accordance with claim 1 wherein $R_2$ is halogen.

3. A steroid in accordance with claim 2 wherein $R_2$ is chlorine.

4. A steroid in accordance with claim 1 wherein $R_3$ is fluorine.

5. A steroid in accordance with claim 1 wherein $R_4$ is β-hydroxymethylene or β-acetyloxymethylene.

6. A steroid in accordance with claim 5 wherein $R_4$ is β-hydroxymethylene.

7. A steroid in accordance with claim 5 wherein $R_4$ is β-acetyloxymethylene.

8. A steroid in accordance with claim 5 wherein $R_5$ is hydrogen.

9. A steroid in accordance with claim 5 wherein $R_3$ is fluorine and $R_5$ is hydrogen.

10. The steroid in accordance with claim 1 having the name 11β-(acetyloxy)-5',6',7',8'-tetrachloro-9-fluoro-2',3'-dihydropregna-1,4-dieno[16α,17-b][1,4]benzodioxin-3,20-dione.

11. The steroid in accordance with claim 1 having the name 11β,21-bis-(acetyloxy)-5',6',7',8'-tetrachloro-9-fluoro-2',3'-dihydropregna-1,4-dieno[16α,17-b][1,4]benzodioxin-3,20-dione.

12. The steroid in accordance with claim 1 having the name 5',6',7',8',21-pentachloro-9-fluoro-2',3'-dihydro-11β-hydroxypregna-1,4-dieno[16α,17-b][1,4]benzodioxin-3,20-dione.

13. The steroid in accordance with claim 1 having the name 21-(acetyloxy)-5',6',7',8'-tetrachloro-9-fluoro-2',3'-dihydro-11β-hydroxypregna-1,4-dieno[16α,17-b][1,4]benzodioxin-3,20-dione.

14. The steroid in accordance with claim 1 having the name 11β-(acetyloxy)-5',6',7',8',21-pentachloro-9-fluoro-2',3'-dihydropregna-1,4-dieno[16α,17-b][1,4]benzodioxin-3,20-dione.

15. The steroid in accordance with claim 1 having the name 5',6',7',8'-tetrachloro-9-fluoro-2',3'-dihydro-11β- hydroxy-21-methoxypregna-1,4-dieno[16α,17-b][1,4]benzodioxin-3,20-dione.
16. A steroid having the formula
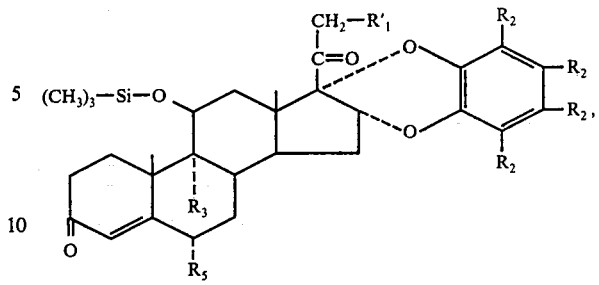
or the 1,2-dehydro derivative thereof, wherein $R'_1$ is hydrogen, halogen or
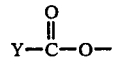
wherein Y is alkyl of 1 to 10 carbon atoms or phenyl;
$R_2$ is halogen or cyano;
$R_3$ is hydrogen or halogen; and
$R_5$ is hydrogen or fluorine.
* * * * *

UNITED STATES PATENT AND TRADEMARK OFFICE
CERTIFICATE OF CORRECTION

PATENT NO. : 4,113,722
DATED : September 12, 1978
INVENTOR(S) : Ravi K. Varma et al It is certified that error appears in the above-identified patent and that said Letters Patent are hereby corrected as shown below:

Column 6, line 14, "-4',6',7',8'-" should read -- -5',6',7',8'- --.

Column 6, line 67 "-116°C." should read -- -115°C.--.

Column 7, line 33, "50 mg" should read --350 mg--.

Signed and Sealed this

Nineteenth Day of December 1978

[SEAL]

Attest:

RUTH C. MASON
Attesting Officer

DONALD W. BANNER
Commissioner of Patents and Trademarks